United States Patent [19]

Bennett

[11] Patent Number: Plant 5,522

[45] Date of Patent: Jul. 30, 1985

[54] MINIATURE ROSE PLANT

[76] Inventor: Cecilia L. D. Bennett, 489 Minot Ave., Chula Vista, Calif. 92010

[21] Appl. No.: 563,276

[22] Filed: Dec. 19, 1983

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by its five-petaled bloom in shades ranging from Persimmon Orange with a bright base of Canary Yellow when newly opened to Blood Red at full maturity.

1 Drawing Figure

The present invention relates to a new and distinct variety of a hardy, dwarf, bush plant of the miniature class; the variety being primarily characterized as an orange blend.

The variety is further characterized by:

Singly petaled (five petals only) bloom, borne singly or in sprays of 3 to 5 or more, held very erect and well above the foliage.

The plant ranges in height from 24 to 36 inches. The canes are sturdy and erect, heavily branched with medium foliage covering. The plant is heavy bloomer that does well in either the green house or outdoors.

The plant is very vigorous with good growth habits, well shaped and attractive in appearance, bearing numerous leaflets of average size.

The seed parent was Orange Honey (Miniature Rose Plant, orange blend; R. S. Moore; introduced by Sequoia Nursery, 1979) and the pollen parent is unknown.

Subsequent to the origination of the variety, I have successfully reproduced it at Tiny Petals Nursery located at aforesaid retaining the distinguishing characteristics through succeeding propagations by cuttings.

The descriptive matter which follows pertains to roses grown and color values observed in plants and newly opened blooms in the months of June and July. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf, bushy, green house or outdoor, garden decoration and single petaled exhibition-quality potted plant.

Class: Miniature.

Variety name: Punkin.

Flowers borne: One to a stem or in sprays of 3 to 5 or more on erect stems with foliage well below the blooms.

Quantity of bloom: Moderate to heavy both outdoors or green house grown.

Bud:

*Peduncle.*—Varies in length from short to long (15 to 50 mm); average diameter and sturdy; medium green with some tinting of bronze.

*Hairs.*—Extremely small and sparse; located over the outer surface of the sepals and on the peduncle, but none on the calyx tube.

*Calyx.*—Color is Scheeles Green (860/1 page 175) with some bronze present in the newer blooms which fades as the hips begin to enlarge.

*Opening.*—Opens well in all weather.

Bloom:

*Size when fully open.*—Average for a miniature variety (40 to 45 mm — $1\frac{1}{2}$ to $1\frac{3}{4}$").

*Petalage.*—Single; five petals only, arranged regularly with no petaloids.

*Form.*—From tight bud to fully opened stage with great rapidity; holding at fully opened until petals fall in final stages of maturity. No reflexing of petals present throughout entire bloom cycle.

Petals: Fairly thick with good substance; matte finish on both the upper and under surfaces.

*Shape.*—Broad obovate form with a slight peak at the apex.

Color: Newly opened flowers from plants grown outdoors (June and July 1983), Chula Vista, Calif.:

*Upper surface.*—Persimmon Orange (710/1 to 710 page 91) with a small area near the base of Buttercup Yellow (5/1 page 5).

*Under surface.*—Persimmon Orange (710/3 page 91) with a small area near the base of Buttercup Yellow (5 page 5).

*General color effect.*—Newly opened flowers - Bright Persimmon Orange with Buttercup Yellow Center. Over a period of 3 to 5 days - Base of petals will fade from dark Buttercup Yellow to pale Buttercup Yellow (5/2 page 5 ) to finally just a tip of the palest shade of Buttercup Yellow (5/3 page 5). The body of the petals will deepen in color from Persimmon Orange (710 page 91) through Marigold Orange (11 page 11) to Dutch Vermilion (717 page 156) and finally Blood Red (820/1 to 820 page 166) before the spent petals drop off cleanly. The under surface of the body fades during the same 3 to 5 days to Buttercup Yellow (5/3 page 5) with an occasional margin of the darker shades of orange and red present on the upper surface at the time.

*Flower longevity.*—(June and July 1983) Plant in pot 1 to 2 days from bud to fully opened bloom. Holding at fully open with brilliant color variations for additional 3 to 5 days before dropping petals. Cut blooms at livingroom temperature 3 to 5 days or longer.

Reproductive organs:

*Stamens.*—A generous amount arranged uniformily around the pistil.

*Filament.*—Varying in lengths.

*Pollen.*—Abundant.

*Pistil.*—Small to average with slight amount of spreading.

*Styles.*—Short and pale yellow in color.

*Ovaries.*—All encased in calyx.

*Hips.*—This cultivar produces hips readily; some enlargement of the calyx tube may even begin before the bloom drops its petals. The hips are Scheeles Green (860/1 page 175) with occasional tint of bronze that appears to fade with the maturing of the hips. Size — Average to large for a miniature variety.

*Seeds.*—6 Or more per hip.

*Sepals.*—Permanent; lanceolate-shaped; recurves against the peduncle as the bloom opens.

Foliage:

*Leaves.*—Average in size with 5 to seven leaflets.

*Leaflets.*—Broad ovate-shaped.

*Margin.*—Very serrated with occasional reddish tinge on the edge, especially noticeable on the newer foliage.

*Color.*—Spinach Green (9060/3 to 0960 page 187) with a tinge of bronze in the newer leaves. The upper surfaces are satiny and the under surfaces have a matte finish of a slightly lighter color than the upper surface.

*Rachis.*—Medium strength; upper side may have a few small hairs; grooved; under side smooth except for a few sparse thorns.

*Stipules.*—Varying in length from short to medium for a miniature; average width; tapering auricles angled outward at about 45 degrees.

Growth:

*Habit.*—Dwarf; bushy; much branched; large for a miniature rose plant, especially a single petaled variety.

*Growth.*—Extremely vigorous.

*Canes.*—Medium to large; sturdy; held very erect.

*Main stems.*—Color — Spinach Green (0960/2 to 0960/3 page 187) with some tinting of bronze, especially noticeable on the newer stems.

*Thorns.*—Few if any on the main stems, becoming very abundant on the branches (averaging 3 to 5 or more from one leaf axil to the next leaf axil on the branch); long and slender; reddish in color; very straight and leaving the branch at about a 90 degree angle. The thorns located on the underside of the rachis are small and narrow; sparse and pale yellow in color and slightly hooked.

*Branches.*—Color — Spinach Green (0960/2 to 0960/3 page 187) with some tinting of bronze. Medium to long in length; sturdy and very erect.

The miniature rose plant and its flowers as herein described may vary in slight detail due to climatic, soil, and cultural conditions under which the variety may be grown; the present description being of the variety as grown at Chula Vista, Calif.

The following is claimed:

1. A new and distinct variety of miniature rose plant of hardy, dwarf, bushy, much branched habit, substantially as illustrated and described, characterized by its single petaled blooms which range in color from Persimmon Orange with a bright Buttercup Yellow base when newly opened to varying shades of Marigold Orange, Dutch Vermilion, and finally Blood Red as the bloom matures; further characterized by an extremely vigorous growth habit, easy to propagate from cuttings, with flowers borne singly and in sprays of 3 to 5 or more.

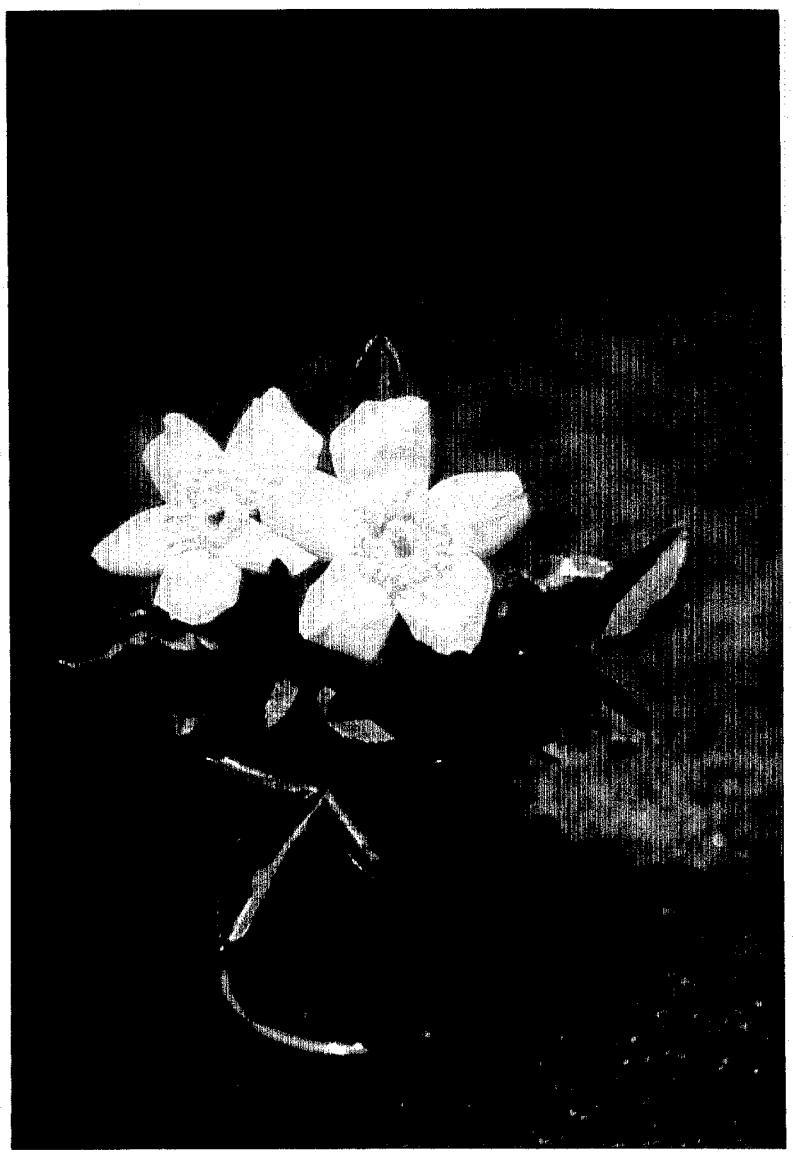

* * * * *